United States Patent
Lee et al.

(10) Patent No.: US 11,325,881 B2
(45) Date of Patent: May 10, 2022

(54) PLASTICIZER COMPOSITION AND PREPARATION METHOD THEREFOR

(71) Applicant: SAMYANG CORPORATION, Seoul (KR)

(72) Inventors: Jae Hoon Lee, Daejeon (KR); Hoon Ryu, Daejeon (KR); Won Hyun Jeon, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 125 days.

(21) Appl. No.: 16/757,138

(22) PCT Filed: Oct. 16, 2018

(86) PCT No.: PCT/KR2018/012192
§ 371 (c)(1),
(2) Date: Apr. 17, 2020

(87) PCT Pub. No.: WO2019/078584
PCT Pub. Date: Apr. 25, 2019

(65) Prior Publication Data
US 2020/0339499 A1 Oct. 29, 2020

(30) Foreign Application Priority Data
Oct. 19, 2017 (KR) .................. 10-2017-0135963

(51) Int. Cl.
| | |
|---|---|
| *C07C 69/013* | (2006.01) |
| *C07C 31/18* | (2006.01) |
| *C07C 69/003* | (2006.01) |
| *C07D 493/04* | (2006.01) |
| *C08L 27/06* | (2006.01) |
| *C07C 67/03* | (2006.01) |
| *C08K 3/22* | (2006.01) |
| *C08K 5/00* | (2006.01) |

(52) U.S. Cl.
CPC ............ *C07C 69/013* (2013.01); *C07C 31/18* (2013.01); *C07C 69/003* (2013.01); *C07D 493/04* (2013.01); *C08L 27/06* (2013.01); *C07C 67/03* (2013.01); *C08K 3/22* (2013.01); *C08K 5/0016* (2013.01)

(58) Field of Classification Search
CPC ..................................... C07C 69/013
See application file for complete search history.

(56) References Cited

U.S. PATENT DOCUMENTS

| | | | |
|---|---|---|---|
| 7,220,710 B2 | 5/2007 | Kunz et al. | |
| 8,722,813 B2 | 5/2014 | Sawada et al. | |
| 2009/0301348 A1* | 12/2009 | Grass | C07D 493/04 106/287.2 |

FOREIGN PATENT DOCUMENTS

| | | |
|---|---|---|
| JP | 2004-537643 A | 12/2004 |
| JP | 2012-62467 A | 3/2012 |
| KR | 10-1079518 B1 | 11/2011 |
| KR | 10-2012-0066904 A | 6/2012 |
| KR | 10-2016-0075922 A | 6/2016 |
| KR | 10-2017-0064071 A | 6/2017 |
| KR | 10-2017-0065055 A | 6/2017 |
| KR | 10-2017-0114269 A | 10/2017 |

OTHER PUBLICATIONS

English Machine Translation for KR20170065055 A obtained Oct. 14, 2021 at https://worldwide.espacenet.com/publicationDetails/biblio?CC=KR&NR=20170065055A&KC=A&FT=D&ND=3&date=20170613&DB=EPODOC&locale=en_EP# (Year: 2017).*
International Search Report issued in PCT/KR2018/012192 (PCT/ISA/210), dated Apr. 10, 2019.

* cited by examiner

*Primary Examiner* — Arrie L Reuther
(74) *Attorney, Agent, or Firm* — Birch, Stewart, Kolasch & Birch, LLP

(57) ABSTRACT

The present invention relates to a plasticizer composition and a preparation method therefor and, more specifically, to a plasticizer composition, which contains an anhydrosugar alcohol monoester, an anhydrosugar alcohol diester, and a sugar alcohol ester at a specific content ratio and has improved plasticity and excellent storage stability, and to a preparation method therefor.

7 Claims, No Drawings

PLASTICIZER COMPOSITION AND PREPARATION METHOD THEREFOR

TECHNICAL FIELD

The present invention relates to a plasticizer composition and a method for preparing the same, and more specifically, a plasticizer composition which comprises anhydrosugar alcohol monoester, anhydrosugar alcohol diester and sugar alcohol ester with specific amount ratios and thus has improved plasticity and excellent storage stability, and a method for preparing the same.

BACKGROUND ART

Hydrogenated sugar (also referred to as "sugar alcohol") means a compound obtained by adding hydrogen to the reductive end group in sugar, and generally has a chemical formula of $HOCH_2(CHOH)_mCH_2OH$ wherein n is an integer of 2 to 5. According to the number of carbon atoms, hydrogenated sugar is classified into tetritol, pentitol, hexitol and heptitol (4, 5, 6 and 7 carbon atoms, respectively). Among them, hexitol having 6 carbon atoms includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, patch adhesive, medicaments such as mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

Korean Laid-open Patent Publication No. 10-2016-0075922 discloses a method for preparing an ester compound by reacting anhydrosugar alcohol and carboxylic acid for use as an additive for resin processing. However, the ester compound prepared thereby needs to be improved in terms of plasticity.

Problems to be Solved

The purpose of the present invention is to provide a plasticizer composition which is prepared by utilizing anhydrosugar alcohol and thus has good eco-friendliness and shows improved plasticity and excellent storage stability, and a method for preparing the same.

Technical Means

In order to achieve the above-stated purpose, the present invention provides a method for preparing a plasticizer composition, comprising the steps of: (1) synthesizing sugar alcohol ester and anhydrosugar alcohol ester by esterification reaction of an alcohol mixture comprising sugar alcohol and anhydrosugar alcohol with carboxylic acid; and (2) neutralizing the resulting mixture obtained in said step (1) comprising sugar alcohol ester and anhydrosugar alcohol ester with basic material, wherein the amount of sugar alcohol in the alcohol mixture used in said step (1) is 5 to 95 parts by weight, based on 100 parts by weight of the mixture of sugar alcohol and anhydrosugar alcohol; and a polyvinylchloride (PVC) resin composition comprising a plasticizer composition prepared by the method and PVC resin.

In another aspect, the present invention provides a plasticizer composition comprising anhydrosugar alcohol monoester, anhydrosugar alcohol diester and sugar alcohol ester, wherein the amount of sugar alcohol ester is 5 to 80 parts by weight, based on 100 parts by weight of the plasticizer composition; and a PVC resin composition comprising the plasticizer composition and PVC resin.

Effect of the Invention

The plasticizer composition provided according to the present invention is prepared by utilizing anhydrosugar alcohol, and thus it has good eco-friendliness and shows improved plasticity and excellent storage stability.

Concrete Mode for Carrying Out the Invention

The present invention is explained in more detail below.

The method for preparing a plasticizer composition of the present invention comprises a step of synthesizing sugar alcohol ester and anhydrosugar alcohol ester by esterification reaction of an alcohol mixture comprising sugar alcohol and anhydrosugar alcohol with carboxylic acid [Step (1)].

The sugar alcohol, also generally referred to as hydrogenated sugar, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials. As the sugar alcohol, preferably hexitol is used, more preferably a sugar alcohol selected from sorbitol, mannitol, iditol or mixtures thereof is used, and even more preferably sorbitol which can be prepared easily through hydrogenation reaction of glucose derived from starch is used.

The anhydrosugar alcohol means any material that is obtained by removing one or more water molecules from sugar alcohol. In the present invention, preferably the anhydrosugar alcohol may be selected from isosorbide (1,6-dianhydrosorbitol), isomannide (1,6-dianhydromannitol), isoidide (1,6-dianhydroiditol) or mixtures thereof, and more preferably isosorbide is used.

The amount of sugar alcohol in the alcohol mixture used in said step (1) is 5 to 95 parts by weight, based on 100 parts by weight of the mixture of sugar alcohol and anhydrosugar alcohol. If the amount of sugar alcohol in 100 parts by weight of the alcohol mixture is less than 5 parts by weight, the plasticity becomes worse. If the amount of sugar alcohol in 100 parts by weight of the alcohol mixture is greater than 95 parts by weight, the storage stability may deteriorate so that white colored substances may be generated during storage of the composition. In an embodiment of the present invention, the amount of sugar alcohol in the alcohol mixture may be 5 to 90 parts by weight, or 10 to 90 parts by weight, or 20 to 90 parts by weight, or 30 to 90 parts by weight, or 40 to 90 parts by weight, based on 100 parts by weight of the mixture of sugar alcohol and anhydrosugar alcohol.

In the present invention, preferably the carboxylic acid may be $C_2$-$C_{24}$ alkyl carboxylic acid, $C_3$-$C_{24}$ cycloalkyl carboxylic acid, $C_6$-$C_{24}$ aryl carboxylic acid, or a mixture thereof. For example, the carboxylic acid may be selected from caprylic acid, caproic acid, lauric acid, octanoic acid, decanoic acid, dodecanoic acid, ethanoic acid (acetic acid), propionic acid, butyric acid, pentanoic acid, hexanoic acid, ethylhexanoic acid, or combinations thereof, but it is not limited thereto.

The esterification reaction of alcohol component with carboxylic acid [Step (1)] may be conducted by using carboxylic acid in an amount of 1 to 2.9 equivalents, preferably 1 to 2.5 equivalents, and more preferably 1 to 2 equivalents, to 1 equivalent amount of alcohol component, although it is not especially limited thereto. If the amount of carboxylic acid used to 1 equivalent amount of alcohol component is less than 1 equivalent, the esterification reaction may be insufficient. If the amount of carboxylic acid used to 1 equivalent amount of alcohol component is greater than 2.9 equivalents, the production cost becomes higher, and the unreacted carboxylic acid component should be removed through distillation and it causes an additional cost for such a further process.

The esterification reaction of alcohol component with carboxylic acid may be conducted in the presence of acid catalyst. As the acid catalyst, an acid catalyst conventionally used in esterification reactions of alcohol may be used, and concretely, an acid catalyst selected from p-toluenesulfonic acid, sulfuric acid, methanesulfonic acid or combinations thereof may be used, but it is not limited thereto. There is no special limitation to the amount of acid catalyst used. Preferably, the esterification reaction may be conducted by using the acid catalyst in an amount of 0.1 to 20 parts by weight, more preferably 0.1 to 10 parts by weight, and even more preferably 0.1 to 5 parts by weight, based on 100 parts by weight of alcohol component. If the amount of acid catalyst used is less than 0.1 part by weight based on 100 parts by weight of alcohol component, the reaction speed may decrease. If the amount of acid catalyst used is greater than 20 parts by weight based on 100 parts by weight of alcohol component, excessive reaction may occur.

There is no special limitation to the conditions of esterification reaction of alcohol component with carboxylic acid. For example, the reaction may be conducted at 70 to 200° C. under 10 to 200 torr in inert atmosphere (for example, in a reactor, inside of which is substituted with nitrogen), but it is not limited thereto.

Water may be contained in the mixture obtained as a result of the esterification reaction, and before conducting the subsequent step, the water may be removed therefrom. This can be conducted by applying vacuum, but it is not limited thereto.

The method for preparing a plasticizer composition of the present invention further comprises a step of neutralizing the resulting mixture obtained in said step (1) comprising sugar alcohol ester and anhydrosugar alcohol ester with basic material [Step (2)].

In the neutralizing step, in order to neutralize the resulting mixture obtained in said step (1), an aqueous solution of basic material such as alkali metal hydroxide, alkaline earth metal hydroxide, or mixture thereof may be used. According to an embodiment, an aqueous solution of NaOH or an aqueous solution of KOH, etc. may be used. There is no special limitation to the amount of aqueous basic solution used, and it may be used in a sufficient amount to neutralize the resulting mixture obtained in said step (1). For example, an aqueous basic solution with pH 10 to 12 may be used in an amount of 50 to 200 parts by weight, and more concretely 50 to 150 parts by weight, based on 100 parts by weight of the resulting mixture obtained in said step (1), but it is not especially limited thereto.

The method for preparing a plasticizer composition of the present invention may further comprise, if necessary, a step of concentrating the neutralized product obtained in said step (2) and a step of filtering and removing salts remaining after the concentration. In addition, the method for preparing a plasticizer composition of the present invention may further comprise, if necessary, a step of further improving the color of the prepared plasticizer composition (for example, active carbon treatment, etc.).

The plasticizer composition prepared by the above method comprises anhydrosugar alcohol monoester, anhydrosugar alcohol diester and sugar alcohol ester.

In an embodiment, the amount of sugar alcohol ester in the plasticizer composition prepared by the above method is 5 to 80 parts by weight, based on 100 parts by weight of the plasticizer composition, and more concretely it may be 5 to 70 parts by weight, or 10 to 70 parts by weight, or 20 to 70 parts by weight, based on 100 parts by weight of the plasticizer composition. The amount of sugar alcohol ester in the plasticizer composition is preferably within the above ranges in terms of improvement of the plasticity and storage stability.

The plasticizer composition prepared by the method of the present invention can exhibit good plasticity for thermoplastic elastomer resin (for example, thermoplastic polyester elastomer, thermoplastic styrene-butadiene elastomer, thermoplastic polyurethane or combinations thereof) or PVC resin.

According to an embodiment of the present invention, the plasticizer composition prepared by the method of the present invention can exhibit good plasticity for PVC. Therefore, the present invention also provides a PVC resin composition comprising a plasticizer composition prepared by the above method and PVC resin.

There is no special limitation to the PVC resin comprised in the above PVC resin composition, and a single conventional PVC resin or a combination of two or more thereof may be used.

Based on 100 parts by weight of the PVC resin, the amount of the plasticizer composition in the PVC resin composition may be 10 parts by weight or more, 20 parts by weight or more, 30 parts by weight or more, or 40 parts by weight or more, and it may be 80 parts by weight or less, 70 parts by weight or less, or 60 parts by weight or less, but it is not limited thereto.

According to another aspect, the present invention provides a plasticizer composition comprising anhydrosugar alcohol monoester, anhydrosugar alcohol diester and sugar alcohol ester, wherein the amount of sugar alcohol ester is 5 to 80 parts by weight, based on 100 parts by weight of the plasticizer composition. This plasticizer composition can be prepared by the above-explained method for preparing a plasticizer composition of the present invention, but it is not limited thereto.

The amount of sugar alcohol ester in the above plasticizer composition is 5 to 80 parts by weight, based on 100 parts by weight of the plasticizer composition. If the amount of sugar alcohol ester in 100 parts by weight of the plasticizer composition is less than 5 parts by weight, the plasticity becomes worse. If the amount of sugar alcohol ester in 100 parts by weight of the plasticizer composition is greater than 80 parts by weight, the storage stability may deteriorate so that white colored substances may be generated during storage of the composition. In an embodiment of the present invention, the amount of sugar alcohol ester in 100 parts by weight of the plasticizer composition may be 5 to 70 parts by weight, or 10 to 70 parts by weight, or 20 to 70 parts by weight.

The above plasticizer composition of the present invention can exhibit good plasticity for thermoplastic elastomer resin (for example, thermoplastic polyester elastomer, thermoplastic styrene-butadiene elastomer, thermoplastic polyurethane or combinations thereof) or PVC resin.

According to an embodiment of the present invention, the plasticizer composition of the present invention can exhibit good plasticity for PVC. Therefore, the present invention also provides a PVC resin composition comprising the above plasticizer composition and PVC resin. The PVC resin comprised in the PVC resin composition and the amount of the plasticizer composition are the same as explained above.

The present invention is explained in more detail through the following Examples and Comparative Examples. However, the scope of the present invention is not limited thereby in any manner.

EXAMPLES

<Preparation of Plasticizer Composition>

Example A1: Preparation of Plasticizer Composition by Using a Mixture of Anhydrosugar Alcohol and Sugar Alcohol, and Fatty Acid 100 g of isosorbide (ISB), 900 g of sorbitol and 1,780 g of caprylic acid were fed into a 3-necked glass reactor and the mixture was agitated at the reactor inside temperature of 110° C. After confirming that the mixture of isosorbide, sorbitol and caprylic acid was dissolved completely, 7 g of para-toluenesulfonic acid as an acid catalyst and 3 g of hypophosphorous acid as a color improving agent were added to the reactor, and then the reactor inside temperature was elevated to 150° C. and the reactor inside pressure was reduced to 120 torr, and the mixture was concentrated for 2 hours, and then the reactor inside temperature was elevated to 180° C. and the reactor inside pressure was increased to 150 torr, and the mixture was concentrated for 4 to 24 hours. When the acid value of the reaction solution became 5 mg/g or less, while maintaining the reactor inside temperature at 75° C., 15 g of potassium hydroxide and 270 g of water were added to the reactor and the mixture was agitated for about 1 hour, and then the organic layer was separated. While maintaining the inside temperature of the separated organic layer at 75° C., the mixture was washed with 300 g of a 10 wt % aqueous solution of sodium sulfate and then concentrated under reduced pressure. The solid product in the concentrate was filtered out to obtain 2,300 g of the plasticizer composition. The obtained plasticizer composition comprised isosorbide monoester, isosorbide diester and sorbitan ester, and the amount of sorbitan ester was 70.0 parts by weight, based on 100 parts by weight of the plasticizer composition.

Example A2: Preparation of Plasticizer Composition by Using a Mixture of Anhydrosugar Alcohol and Sugar Alcohol, and Fatty Acid 2,400 g of a plasticizer composition was prepared by the same method as in Example A1, excepting that the amount of isosorbide was changed from 100 g to 600 g, the amount of sorbitol was changed from 900 g to 400 g, and the amount of caprylic acid was changed from 1,780 g to 1,870 g. The obtained plasticizer composition comprised isosorbide monoester, isosorbide diester and sorbitan ester, and the amount of sorbitan ester was 26.2 parts by weight, based on 100 parts by weight of the plasticizer composition.

Example A3: Preparation of Plasticizer Composition by Using a Mixture of Anhydrosugar Alcohol and Sugar Alcohol, and Fatty Acid 2,500 g of a plasticizer composition was prepared by the same method as in Example A1, excepting that the amount of isosorbide was changed from 100 g to 950 g, the amount of sorbitol was changed from 900 g to 50 g, the amount of caprylic acid was changed from 1,780 g to 1,980 g, the amount of potassium hydroxide was changed from 15 g to 14 g, and the amount of water was changed from 270 g to 280 g. The obtained plasticizer composition comprised isosorbide monoester, isosorbide diester and sorbitan ester, and the amount of sorbitan ester was 5.0 parts by weight, based on 100 parts by weight of the plasticizer composition.

Example A4: Preparation of Plasticizer Composition by Using a Mixture of Anhydrosugar Alcohol and Sugar Alcohol, and Fatty Acid Mixture (C8/C10)

2,500 g of a plasticizer composition was prepared by the same method as in Example A1, excepting that the amount of isosorbide was changed from 100 g to 600 g, the amount of sorbitol was changed from 900 g to 400 g, and 1,920 g of fatty acid mixture (containing caprylic acid (C8) and decanoic acid (C10) with a C8:C10 weight ratio of 6:4) was used instead of 1,780 g of caprylic acid. The obtained plasticizer composition comprised isosorbide monoester, isosorbide diester and sorbitan ester, and the amount of sorbitan ester was 25.4 parts by weight, based on 100 parts by weight of the plasticizer composition.

Example A5: Preparation of Plasticizer Composition by Using a Mixture of Anhydrosugar Alcohol and Sugar Alcohol, and Fatty Acid Mixture (C6/C12)

2,400 g of a plasticizer composition was prepared by the same method as in Example A1, excepting that the amount of isosorbide was changed from 100 g to 600 g, the amount of sorbitol was changed from 900 g to 400 g, and 1,920 g of fatty acid mixture (containing caproic acid (C6) and lauric acid (C12) with a C6:C12 weight ratio of 6:4) was used instead of 1,780 g of caprylic acid. The obtained plasticizer composition comprised isosorbide monoester, isosorbide diester and sorbitan ester, and the amount of sorbitan ester was 24.7 parts by weight, based on 100 parts by weight of the plasticizer composition.

Comparative Example A1: Preparation of Plasticizer Composition by Using Anhydrosugar Alcohol and Fatty Acid 2,300 g of a plasticizer composition was prepared by the same method as in Example A1, excepting that the amount of isosorbide was changed from 100 g to 1,000 g, the amount of sorbitol was changed from 900 g to 0 g, the amount of caprylic acid was changed from 1,780 g to 1,920 g, the amount of potassium hydroxide was changed from 15 g to 14 g, and the amount of water was changed from 270 g to 280 g. The obtained plasticizer composition comprised isosorbide monoester and isosorbide diester, but the amount of sorbitan ester was 0 part by weight, based on 100 parts by weight of the plasticizer composition.

Comparative Example A2: Preparation of Plasticizer Composition by Using a Mixture of Anhydrosugar Alcohol and Sugar Alcohol, and Fatty Acid 2,520 g of a plasticizer composition was prepared by the same method as in Example A1, excepting that the amount of isosorbide was changed from 100 g to 970 g, the amount of sorbitol was changed from 900 g to 30 g, and the amount of caprylic acid was changed from 1,780 g to 2,011 g. The obtained plasticizer composition comprised isosorbide monoester, isosorbide diester and sorbitan ester, and the amount of sorbitan ester was 2.2 parts by weight, based on 100 parts by weight of the plasticizer composition.

Comparative Example A3: Preparation of Plasticizer Composition by Using Sugar Alcohol and Fatty Acid 2,200 g of a plasticizer composition was prepared by the same method as in Example A1, excepting that the amount of isosorbide was changed from 100 g to 0 g, the amount of sorbitol was changed from 900 g to 1,000 g, and the amount of caprylic acid was changed from 1,780 g to 1,620 g. The obtained plasticizer composition comprised isosorbide monoester, isosorbide diester and sorbitan ester, and the amount of sorbitan ester was 85.8 parts by weight, based on 100 parts by weight of the plasticizer composition. During storage of the plasticizer composition at room temperature for 7 days or longer, white colored precipitate was generated.

<Preparation of Polyvinylchloride (PVC) Paste>

Examples B1 to B5, Comparative Examples B1 to B3 and Reference Example 1

In order to compare the plasticizing efficiencies of the plasticizer compositions prepared in the above Examples and Comparative Examples, 100 parts by weight of PVC resin and 60 parts by weight of each of the plasticizer compositions prepared in the above Examples A1 to A5 and Comparative Examples A1 to A3 were mixed and agitated to prepare PVC pastes of Examples B1 to B5 and Comparative Examples B1 to B3, respectively. In addition, 100 parts by weight of PVC resin and 60 parts by weight of conventional plasticizer, dioctyl phthalate (GL-100, LG Chem) were mixed and agitated to prepare a PVC paste of Reference Example 1.

The properties of the PVC pastes prepared above were measured by the methods explained below, and the results are shown in the following Table 2.

(1) Viscosity: The viscosities of the PVC pastes were measured by using Brookfield viscometer.

(2) Precipitate generation: Whether precipitate was generated or not was confirmed by naked eye after storage of the plasticizer compositions at room temperature for 7 days.

X: No precipitate generated
O: Precipitate generated

TABLE 1

The amounts of ISB and sorbitol used and the compositional ratio of the resulting plasticizer composition

|  | ISB amount (g) | Sorbitol amount (g) | Fatty acid | Sorbitan ester amount (parts by weight) | ISB diester amount (parts by weight) | ISB monoester amount (parts by weight) |
|---|---|---|---|---|---|---|
| Example A1 | 100 | 900 | Caprylic acid (C8) | 70.0 | 13.0 | 7.4 |
| Example A2 | 600 | 400 | Caprylic acid (C8) | 26.2 | 60.3 | 6.1 |
| Example A3 | 950 | 50 | Caprylic acid (C8) | 5.0 | 82.2 | 5.7 |
| Example A4 | 600 | 400 | C8/C10 Fatty acid mixture | 25.4 | 59.6 | 5.9 |
| Example A5 | 600 | 400 | C6/C12 Fatty acid mixture | 24.7 | 58.3 | 7.9 |
| Comparative Example A1 | 1,000 | 0 | Caprylic acid (C8) | 0 | 94.7 | 1.8 |
| Comparative Example A2 | 970 | 30 | Caprylic acid (C8) | 2.2 | 89.9 | 5.0 |
| Comparative Example A3 | 0 | 1,000 | Caprylic acid (C8) | 85.8 | 5.1 | 4.2 |

ISB: Isosorbide

In the above Table 1, the amounts of ISB diester, ISB monoester and sorbitan ester represent their weight ratio compared with 100 parts by weight of the plasticizer composition. In 100 parts by weight of the plasticizer composition, as well as the ISB diester, ISB monoester and sorbitan ester, impurities are contained in remainder amount.

TABLE 2

The results of measuring the properties of the PVC paste

|  | Example | | | | | Comparative Example | | | Reference Example |
|---|---|---|---|---|---|---|---|---|---|
|  | B1 | B2 | B3 | B4 | B5 | B1 | B2 | B3 | 1 |
| PVC resin (parts by weight) | 100 | 100 | 100 | 100 | 100 | 100 | 100 | 100 | 100 |
| Plasticizer (parts by weight) | Example A1 (60) | Example A2 (60) | Example A3 (60) | Example A4 (60) | Example A5 (60) | Comparative Example A1 (60) | Comparative Example A2 (60) | Comparative Example A3 (60) | GL-100 (60) |
| Sorbitan ester amount (parts by weight) | 70.0 | 26.2 | 5.0 | 25.4 | 24.7 | 0 | 2.2 | 85.8 | — |
| Viscosity ($\times 10^4$, Pa·s) | 1.27 | 1.32 | 1.35 | 1.31 | 1.32 | 1.51 | 1.48 | 1.25 | 1.35 |
| Precipitate generation | X | X | X | X | X | X | X | O | — |

GL-100 (LG Chem): dioctyl phthalate-based plasticizer

As described in the above Table 2, the PVC pastes of Examples B1 to B5 prepared by using the plasticizer compositions according to the present invention exhibited the same or superior plasticity as compared with the conventional plasticizer (GL-100), and even after storage at room temperature for 7 days or longer, they did not cause any problem of non-uniformity of composition due to generation of white colored precipitate.

However, the PVC pastes of Comparative Examples B1 (containing no sorbitan ester) and B2 (containing 2.2 parts by weight of sorbitan ester) prepared by using the plasticizer compositions containing less than 5 parts by weight of sorbitan ester exhibited inferior plasticity as compared with the conventional plasticizer (GL-100), and the PVC paste of Comparative Example B3 (containing 85.8 parts by weight of sorbitan ester) prepared by using the plasticizer composition containing greater than 80 parts by weight of sorbitan ester exhibited the same or superior plasticity as compared with the conventional plasticizer (GL-100), but after storage at room temperature for 7 days or longer, white colored precipitate was generated in the composition and thus it was not suitable for application as a plasticizer.

The invention claimed is:

1. A method for preparing a plasticizer composition, comprising the steps of:
   (1) synthesizing sugar alcohol ester and anhydrosugar alcohol ester by esterification reaction of an alcohol mixture comprising sugar alcohol and anhydrosugar alcohol with carboxylic acid; and
   (2) neutralizing the resulting mixture obtained in said step (1) comprising sugar alcohol ester and anhydrosugar alcohol ester with basic material,
   wherein the amount of sugar alcohol in the alcohol mixture used in said step (1) is 20 to 90 parts by weight, based on 100 parts by weight of the mixture of sugar alcohol and anhydrosugar alcohol.

2. The method for preparing a plasticizer composition of claim 1, wherein the sugar alcohol is selected from sorbitol, mannitol, iditol or mixtures thereof.

3. The method for preparing a plasticizer composition of claim 1, wherein the anhydrosugar alcohol is selected from isosorbide, isomannide, isoidide or mixtures thereof.

4. The method for preparing a plasticizer composition of claim 1, wherein the carboxylic acid is $C_2$-$C_{24}$ alkyl carboxylic acid, $C_3$-$C_{24}$ cycloalkyl carboxylic acid, $C_6$-$C_{24}$ aryl carboxylic acid, or a mixture thereof.

5. The method for preparing a plasticizer composition of claim 1, wherein the basic material is alkali metal hydroxide, alkaline earth metal hydroxide, or a mixture thereof.

6. A PVC resin composition comprising a plasticizer composition prepared by the method of claim 1; and PVC resin.

7. The PVC resin composition according to claim 6, wherein the plasticizer composition comprises anhydrosugar alcohol monoester, anhydrosugar alcohol diester and sugar alcohol ester, wherein the amount of sugar alcohol ester is 20 to 70 parts by weight, based on 100 parts by weight of the plasticizer composition.

* * * * *